United States Patent
Menz et al.

(10) Patent No.: US 7,115,141 B2
(45) Date of Patent: Oct. 3, 2006

(54) DEVICE FOR SUPPORTING A SURGICAL STEP IN A VESSEL, PARTICULARLY FOR REMOVAL AND IMPLANTATION OF HEART VALVES

(75) Inventors: Wolfgang Menz, Dettenheim (DE); Andreas Schoth, Merdingen (DE)

(73) Assignees: Universitatsklinikum Freiburg, Freiburg (DE); Albert-Ludwigs-Universitat, Freiburg (DE)

( * ) Notice: Subject to any disclaimer, the term of this patent is extended or adjusted under 35 U.S.C. 154(b) by 192 days.

(21) Appl. No.: 09/971,580

(22) Filed: Oct. 9, 2001

(65) Prior Publication Data

US 2002/0128702 A1 Sep. 12, 2002

(30) Foreign Application Priority Data

Oct. 9, 2000 (DE) .......................... 100 49 814

(51) Int. Cl.
*A61F 2/06* (2006.01)

(52) U.S. Cl. ..................... 623/1.12; 623/1.15
(58) Field of Classification Search ......... 623/1.1–1.53, 623/900; 606/191–195, 200, 108, 1
See application file for complete search history.

(56) References Cited

U.S. PATENT DOCUMENTS

| | | | | |
|---|---|---|---|---|
| 5,098,440 A | * | 3/1992 | Hillstead | 606/108 |
| 5,167,614 A | * | 12/1992 | Tessmann et al. | 623/1.15 |
| 5,411,507 A | * | 5/1995 | Heckele | 606/108 |
| 5,423,885 A | * | 6/1995 | Williams | 623/1.17 |
| 5,441,515 A | * | 8/1995 | Khosravi et al. | 606/194 |
| 5,474,563 A | * | 12/1995 | Myler et al. | 606/108 |
| 5,618,299 A | * | 4/1997 | Khosravi et al. | 62/1.2 |
| 5,643,309 A | * | 7/1997 | Myler et al. | 623/1.15 |
| 5,843,027 A | | 12/1998 | Stone et al. | |
| 5,941,895 A | * | 8/1999 | Myler et al. | 606/195 |
| 6,015,430 A | | 1/2000 | Wall | |
| 6,027,508 A | * | 2/2000 | Ren et al. | 606/108 |
| 6,027,509 A | * | 2/2000 | Schatz et al. | 606/108 |
| 6,036,723 A | | 3/2000 | Anidjar et al. | |
| 6,165,209 A | * | 12/2000 | Patterson et al. | 623/1.1 |
| 6,187,016 B1 | * | 2/2001 | Hedges et al. | 606/108 |
| 2002/0188344 A1 | * | 12/2002 | Bolea et al. | 623/1.11 |

FOREIGN PATENT DOCUMENTS

| | | |
|---|---|---|
| DE | 19904975 | 9/2000 |
| EP | 0621015 | 10/1994 |
| EP | 0732088 | 9/1996 |
| EP | 0852933 | 7/1998 |

* cited by examiner

*Primary Examiner*—Michael J. Milano
*Assistant Examiner*—Tan-Uyen (Jackie) T. Ho
(74) *Attorney, Agent, or Firm*—Antonelli, Terry, Stout & Kraus, LLP

(57) ABSTRACT

A device is disclosed for assisting surgical operations inside a vessel, particularly for the minimally invasive explantation and implantation of cardiac valves, comprising an operating structure adapted to be implanted within the vessel, that is adapted to be fixedly and detachably joined to the inner wall of the vessel and is provided with at least one connector and/or support structure for a further instrument required for the surgical operation.

15 Claims, 3 Drawing Sheets

DEVICE FOR SUPPORTING A SURGICAL STEP IN A VESSEL, PARTICULARLY FOR REMOVAL AND IMPLANTATION OF HEART VALVES

BACKGROUND OF THE INVENTION

1. Field of the Invention

The present invention relates to a device for assisting surgical operations inside a vessel, particularly for the minimally invasive explantation and implantation of cardiac valves for ablation of an artic valve on the human heart by a minimally invasive surgical operation.

2. Description of the Prior Art

The malfunctioning of an aortic valve results in cardiac insufficiency and hence in a situation that is potentially fatal for the patient. For repair of such a defect, artificial aortic valves have been developed which are implanted as a substitute for the damaged valve in complex and risky open-heart surgery (sternotomy). The operation becomes particularly difficult when there is strong calcareous degeneration on the natural valve because painstaking attention must be paid during removal in order to ensure that calcification particles will not enter the blood circulation and cause there thromboses at other sites in the body. It is common to fasten the replacement valves which are either mere engineering products or derived from porcine valves by suturing in the place of the removed valve.

There are numerous approaches in the development of methods simplifying this complex procedure of aortic-valve replacement in terms of both the surgical technique and the discomfort and strain for the patient, aiming at a minimally invasive technique of replacement of the aortic valve. In these approaches, the operation is performed via the femoral artery or even through the groin.

In view of the very restricted possibilities of access in the aortic arch, it is inevitable to adopt complex surgical strategies, firstly for explantation of the calcified artic valve and secondly for the implantation of an artificial valve in situ. Apart from all difficulties involved in the surgical operation even though minimally invasive surgery is concerned that operates on advanced catheter technology the surgeon is required to apply a maximum of concentration and above all a steady hand, specifically because the individual steps of surgical handling are within the millimetre range and therebelow. With the minimally invasive operation being performed with a sustained natural function of the heart, it is moreover important to carry out the operation as quickly as possible in order to keep the strain on the cardiac system at a minimum, which means that an operation of this kind is performed under a certain pressure in terms of time.

SUMMARY OF THE INVENTION

The present invention provides an aid that can substantially facilitate the performance of the minimally invasive operation, by a surgeon performing surgical operations inside a vessel, particularly in the performance of a minimally invasive explantation and implantation of cardiac valves. Namely, a surgical operation carried out within an operating zone that encompasses only a few millimetres of operating site and hence demands a maximum of concentration on the surgeon's part. In particular, the invention substantially facilitates the operation of advanced surgical tools such as catheter tools or the like within the operating site and thus reduces the duration of the surgical operation, which at the same time provides at a substantial reduction of the strain on the patient.

In accordance with the present invention the device for assisting surgical operations inside a vessel, particularly for the minimally invasive explantation and implantation of cardiac valves comprises an operating structure for implantaton inside the vessel and to be joined tightly and detachably on the inner wall of the vessel, The operating structure moreover comprises at least one connector and/or support structure for a further instrument required for the surgical operation.

The invention initially establishes an operating structure at the operating site, which is fixedly anchored in the surrounding tissue wall and presents, due to its geometry, a reference structure for the topographic reference in all subsequent manipulations. This reference structure may have the shape of an unfoldable cylinder, for example, which is provided with a bayonet catch. This fixedly installed structure now permits the defined positioning of subsequently introduced tools by fixed coupling. These instruments may be cutting, coagulating or observation instruments. After the actual application, the used instrument may be uncoupled from the bayonet catch of the operating structure for removal whereupon the operating structure is ready for receiving a further instrument. This instrument has again a known relationship to the previously used instrument or tool.

In the case of replacement of the aortic valve it is possible in this manner to locate, measure and ablate initially the defective and/or calcareous valve—possibly in several successive steps and with different tools. The new valve is then equally introduced in a minimally invasive operation and fixed in the desired position, with employment of the operating structure. In the case of malfunctioning or of excessive wear, this valve could be replaced by a third valve in a comparatively simple manner, again with use of the bayonet catch and with application of suitable catheter tools. This system could be used to treat a patient at regular intervals with a valve corresponding to the latest state of the art.

As the operating structure is equally introduced into the vessel in a minimally invasive operation, it is preferably designed to be foldable so as to allow for transportation through a narrow vesicular duct, for example, a narrow artery.

In an expedient embodiment, the operating structure, too, may be conveyed to the aorta in several parts and composed there.

An embodiment of the operating structure is a resilient, preferably highly elastic sheet that is folded for transport and conveyed to the implantation site inside a sleeve. There, the sheet is ejected from the sleeve by means of a ram and then unfolds automatically due to the elastic forces. Recesses or knops are provided on the sheet, which constitute a bayonet-like catch so that subsequently introduced structures such as catheter tools can be fixed on the operating structure in a simple manner and can be detached and retracted again in an equally simple manner, The sheet, which has preferably a rectangular shape, presents a respective lock seam on the edges extending in parallel with the cylinder axis so that the opposing lock seams will automatically mutually engage and hence constitute a defined cylinder.

On the outside surface of the cylinder, moreover spikes are mounted which are so designed that they compensate the irregular lumen of the aorta and may be hooked in the tissue wall of the vessel. As the spikes do not project orthogonally from the cylinder wall but extend at an angle in a rearward direction the operating structure can only be shifted in the forward direction and is engaged in the tissue wall only is pushed back or when the blood stream passes corresponding forces onto the spikes.

With such an arrangement an individual adaptation to the biologic conditions of the aorta, on the one hand, and a precise reference area for the engineering components, on the other hand, are achieved at the same time. To this adds that despite the introduced processing equipment the spacers of the spikes ensure a certain fluidic passage through the aorta, which means that the spikes space the cylinder from the aorta wall so that a blood stream will be ensured between the aorta and the cylinder.

For the permanent implantation of an artificial cardiac valve the structure serves to fix and receive the flow forces while the sealing of the valve against the vesicular wall may be implemented independently and separately of the holding forces.

BRIEF DESCRIPTION OF THE DRAWINGS

The following is a description of the present invention by exemplary embodiments, without any limitation of the invention, with reference to the drawing wherein.

DESCRIPTION OF THE PREFERRED EMBODIMENT OF THE INVENTION

Figure 1A:
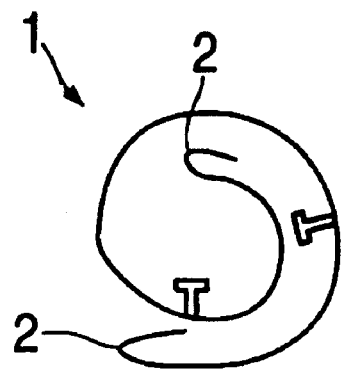
FIG. 1a is a cross view of an operating structure having a sheet-like configuration in a coiled condition.
Figure 1B:
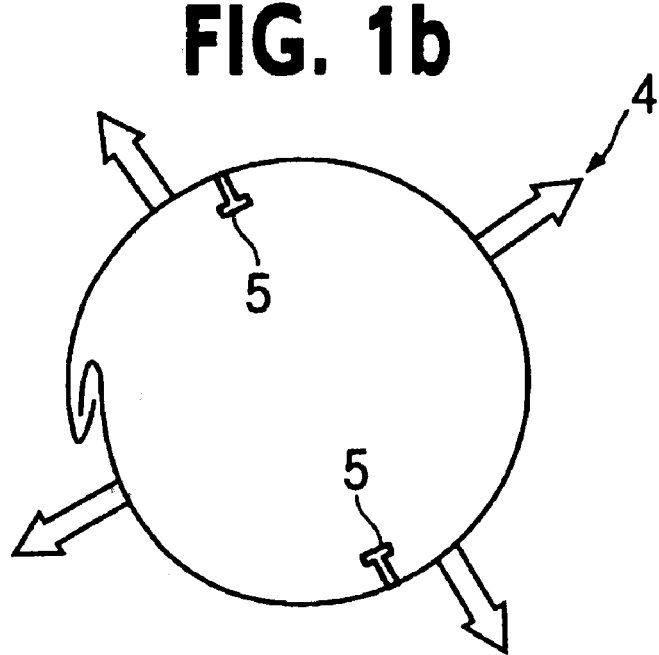
FIG. 1b is a cross view of an operating structure having a sheet-like configuration in an unwound condition.

The operating structure 1 illustrated in FIGS. 1a and 1b is a resilient sheet material, for example a synthetic or metal sheet that is coiled about a longitudinal axis as is shown in FIG. 1a. In this condition, the sheet material of the operating structure 1 presents a bias in such a way that the coiled operating structure would automatically resume an unwound condition due to the inherent bias, as becomes evident from FIG. 1b, for example, unless an external constraint ensures the compressed or coiled condition of the operating structure 1.

The material of which the operating structure 1 is made may also be a braided material, for instance braided synthetic or metalfibers, in addition to the aforementioned variant.

Figure 2A:
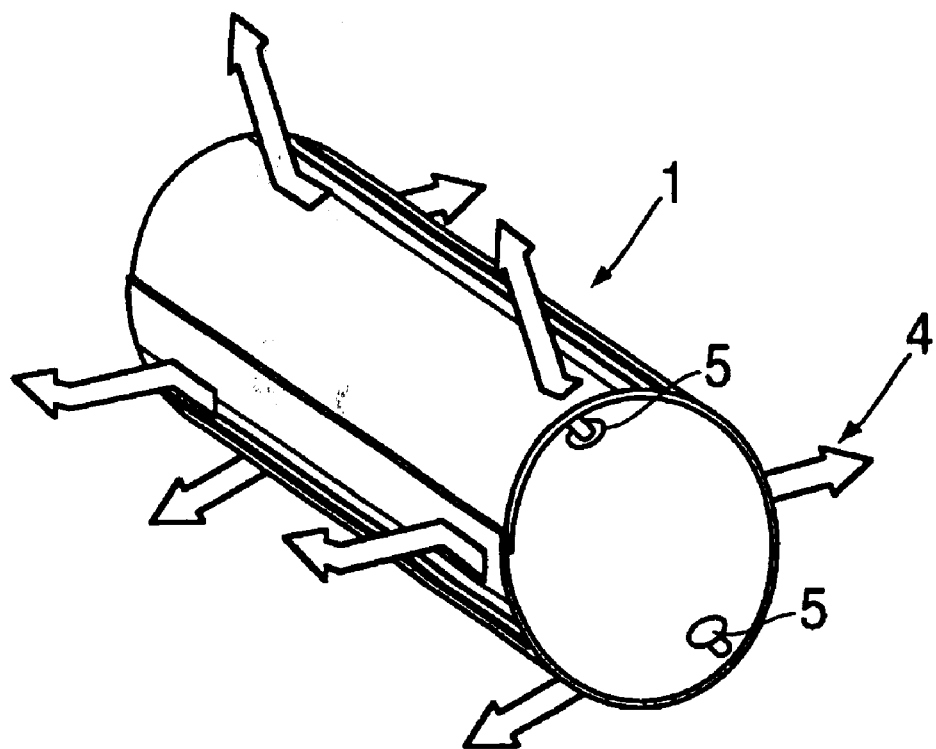
FIG. 2a is a perspective illustration of an unfolded operating structure.
Figure 2B:
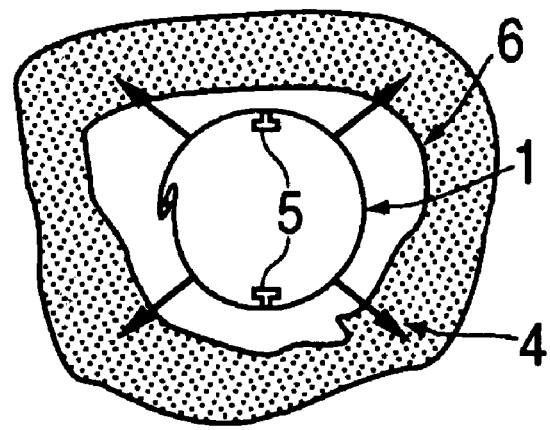
FIG. 2b is a schematic cross-section view of an operating structure inside a vessel.

To ensure the condition that a complete hollow cylinder is locked in place as illustrated in FIG. 2b, seams 2 and 3 are provided in the edge zones of the sheet material of the operating structure 1. The seams 2 and 3 are so configured to appropriately mutually engage in the unwound locked condition, as may be seen in FIG. 1b. The diameter of the hollow cylinder of the operating structure 1, which is formed in this manner, should be approximately matched with the inner diameter of the vessel section adjacent to the region that requires surgical treatment. in order to ensure that the operating structure can be implanted inside the vessel with a maximum of non-slip or stationary fixation anchoring elements 4 in the form of spikes are provided on the outside surface of the sheet material of the operating structure 1, which spikes are oriented at an angle from the surface of the operating structure 1. The oblique position of the spikes—which may preferably be designed in the form of barbs—permits the advance of the unfolded operating structure 1 inside a vessel in one direction while it prevents at the same time a displacement in the opposite direction. The fixation of the operating structure inside the vessel requires a small rearward movement so that the anchoring elements 4 can be stationarily anchored in the vesicular wall.

Moreover, the operating structure 1 is provided with knops 5 projecting into the interior of the cylinder, which are configured in the manner of a bayonet catch. The use of the bayonet catch permits a fixed detachable connection of further catheter tools or surgical instruments to the operating structure that is fixedly installed in the vessel, so that certain surgical operations can be performed in situ. With the operating structure 1 implanted within the vessel, the operating surgeon achieves a stationary reference point that permits a safer and more rapid performance of the surgical operation, specifically as adjusting operations within the surgical site, which is only in the millimetre range, can be carried out more quickly and in a safer manner. Apart therefrom, the operating structure contributes to a reduction of the strain on the operating surgeon in terms of concentration.

FIG. 2a illustrates a perspective view of the unfolded operating structure I that is shaped in the form of a hollow cylinder. There, anchoring elements 4 can be seen which are mounted on the outside wall of the operating structure I at an inclination relative to the surface. The knops 5, serving as a bayonet catch means, are visible in the interior space of the hollow cylinder.

FIG. 2b shows a cross-sectional view taken through an operating structure I anchored inside the vessel 6, with the structure being fixedly connected to the vesicular wall 6 via the anchoring element 4. What can be clearly seen in this schematic illustration is the spacing between the cylinder and the vesicular wall, which ensures a retained blood stream through the space therebetween.

Figure 3A:
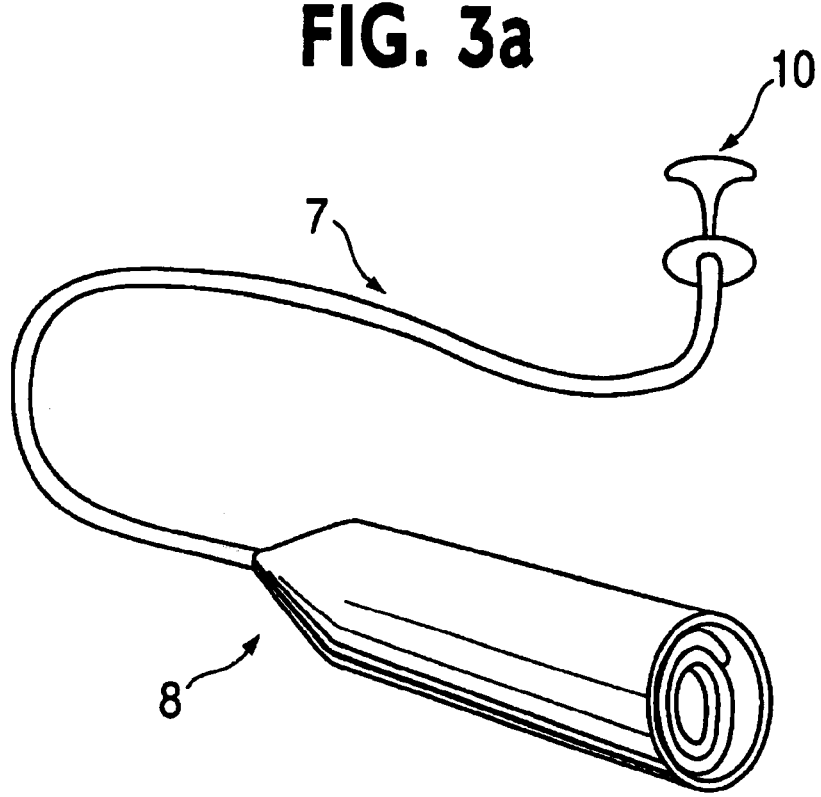
FIGS. 3a and 3b are schematic illustrations of a sleeve-type catheter for introduction of the operating structure into a vessel.
Figure 3B:
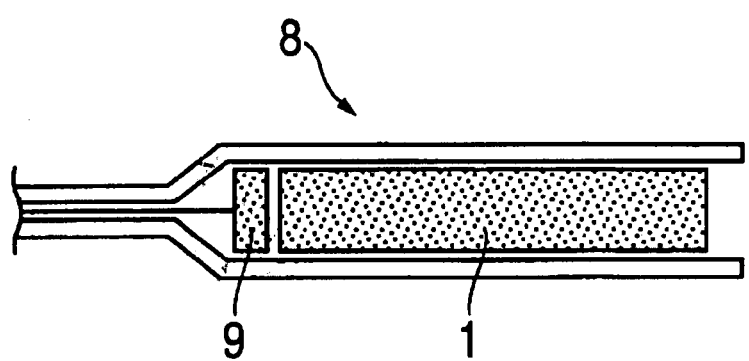

A sleeve-type or hollow catheter 7 is provided which is shown in more details in FIGS. 3a and 3b—for the introduction of an operating structure in accordance with the invention inside the vessel, for example in the vicinity of the aortic valves within the aortic arch, which are to be replaced by the surgical operation. The sleeve-type catheter 7 comprises a transporting sleeve 8 on its distal end, into which the compressed operating structure 1 can be inserted. In the cross-sectional view according to FIG. 3b, the compressed or coiled operating structure 1 is contained within the transporting sleeve 8. The compressed operating structure 1 can then be pushed out of the transporting sleeve 8 by means of a plunger structure 9 that is configured as ram on the distal side and connected to a manual operating element 10 on the proximal side; then the ejected operating structure can be deposited at a suitable site in the vessel.

With the aforedescribed operating structure it is hence possible for the first time to create a permanent fixing aid inside a vessel for further surgical catheter tools, which permits a simpler, more rapid and safer realization of complex surgery performed as minimally invasive operations. With the operating structure of the invention, it is possible in particular to perform the complex surgery on cardiac valves in a safer and more rapid operation.

LIST OF REFERENCE NUMERALS 1 operating structure
2 and 3 lateral edges of the sheet material of the operating structure
4 anchoring elements
5 knops, bayonet catch
6 vesicular wall
7 sleeve-type hollow catheter
8 transporting sleeve
9 plunger structure
10 manual operating element

What is claimed is:

1. A device for assisting surgical operations inside a vessel, including minimally invasive explanation and implantation of cardiac valves, comprising:
   an operating structure which is implanted within the vessel, which is fixedly and detachably joined to an inner wall of the vessel and is provided with at least one connector and/or support structure for a further instrument required for the surgical operation; and wherein
   the operating structure unfolds or uncoils and assumes a shape of a cylinder in an unfolded or uncoiled condition, the cylinder having a diameter smaller than a diameter of the vessel, the operating structure is configured as a coiled sheet element presenting two edges extending in parallel with an axis of the cylinder, and a respective lock seam or fold is formed on the two edges so that opposing lock seams are mutually engaged and contribute to a dimensionally stable cylinder shape of the operating structure.

2. A device according to claim 1, wherein the operating structure comprises a windable sheet or an extensible mesh.

3. A device according to claim 1, wherein the operating structure is a shape-memory metal.

4. A device according to claim 1, wherein the operating structure has an outer surface facing the inner wall of the vessel, on which anchoring elements are provided for being anchored in the surface of the vessel.

5. A device according to claim 4, wherein the anchoring elements are arranged at an angle α different than 90° from the surface of the operating structure so that the operating structure is displaceable in a preferred direction inside the vessel but not in an opposite direction thereof.

6. A device according to claim 1, wherein the operating structure has an inside surface on which the connector and/or support structure is provided.

7. A device according to claim 1, wherein the connector and/or support structure is a cut-out in a wall of the cylinder, as a recess or a knop.

8. A device according to claim 1, wherein the connector structure is a plug-in or bayonet-catch connector for fixing or connecting thereon further surgical instruments or for connecting at least one further operating structure.

9. A device according to claim 1, wherein in a folded or coiled condition, the operating structure is inserted into a sleeve-type or hollow catheter for carrying the operating structure into a vicinity of a vesicular site to be treated.

10. A device according to claim 9, wherein a ram-like pusher device is provided for ejecting the operating structure from a sleeve-type or hollow catheter, which the ram-like pusher device carries the operating structure out of the catheter into the vessel.

11. A device according to claim 1 wherein the operating structure has an outer surface facing the inner wall of the vessel, on which anchoring elements are provided for being anchored in the surface of the vessel.

12. A device according to claim 11, wherein the anchoring elements are barbs.

13. A device according to claim 11, wherein the anchoring elements are arranged at an angle α different than 90° from the surface of the operating structure so that the operating structure is displaceable in a preferred direction inside the vessel but not in an opposite direction thereof.

14. A device according to claim 11, wherein the operating structure is configured as coiled sheet element presenting two edges extending in parallel with an axis of the cylinder; and
   a respective lock seam or fold is formed on edges so that opposing lock seams are mutually engaged and contribute to a dimensionally stable cylinder shape of the operating structure.

15. A device according to claim 1 wherein the at least one connector and/or support structure is a cut-out in a wall of the cylinder as a recess or a knop.

* * * * *

UNITED STATES PATENT AND TRADEMARK OFFICE
CERTIFICATE OF CORRECTION

PATENT NO. : 7,115,141 B2 Page 1 of 1
APPLICATION NO. : 09/971580
DATED : October 3, 2006
INVENTOR(S) : Wolfgang Menz and Andreas Schoth It is certified that error appears in the above-identified patent and that said Letters Patent is hereby corrected as shown below:

Title Page, add at (75) Inventors: Friedhelm Beyersdorf, Freiburg (DE) and Geog Lutter, Kiel (DE).

Signed and Sealed this

Twentieth Day of February, 2007

JON W. DUDAS
*Director of the United States Patent and Trademark Office*